United States Patent [19]

Matsuda et al.

[11] 4,115,437

[45] Sep. 19, 1978

[54] SULFONATED PRODUCT OF BUTADIENE OR ISOPRENE OLIGOMER AND THE PRODUCTION THEREFOR

[75] Inventors: Yoshinobu Matsuda, Ibaraki; Yukio Suzuki, Toyonaka; Seimei Yasui, Takarazuka, all of Japan

[73] Assignee: Sumitomo Chemical Company, Limited, Osaka, Japan

[21] Appl. No.: 833,654

[22] Filed: Sep. 15, 1977

[30] Foreign Application Priority Data

Oct. 28, 1976 [JP] Japan .................. 51-130135
Nov. 11, 1976 [JP] Japan .................. 51-135934

[51] Int. Cl.² ............... C07C 143/16; C11D 1/14
[52] U.S. Cl. .................................. 260/513 R; 210/58; 252/555; 260/513 B; 260/683.15 D
[58] Field of Search .................. 260/513 B, 513 R

[56] References Cited

U.S. PATENT DOCUMENTS

| | | | |
|---|---|---|---|
| 2,384,969 | 9/1945 | Serniuk | 260/513 R |
| 3,356,717 | 12/1967 | Furrow | 260/513 B |
| 3,424,770 | 1/1969 | Stein et al. | 260/513 B |
| 4,070,396 | 1/1978 | Convers et al. | 260/513 B |

FOREIGN PATENT DOCUMENTS

49-6,834 1/1974 Japan.

*Primary Examiner*—Joseph E. Evans
*Attorney, Agent, or Firm*—Birch, Stewart, Kolasch and Birch

[57] ABSTRACT

A sulfonated product of butadiene or isoprene oligomer of the formula:

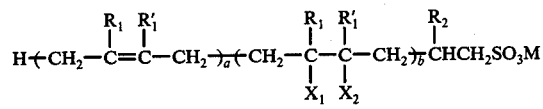

wherein one of $R_1$ and $R_1'$ is hydrogen or methyl and another one is hydrogen; $R_2'$ is hydrogen or methyl; one of $X_1$ and $X_2$ is $-SO_3M$ and another one is hydrogen; $a$ and $b$ are each an integer satisfying the conditions; $n = a + b$, $2 \leq n \leq 40$ and $0 \leq b$; M is hydrogen, Na, K, Li or $-NR_3R_4R_5R_6$; and $R_3$, $R_4$, $R_5$ and $R_6$ are each hydrogen or an alkyl having 1 to 6 carbon atoms, which has specific properties, particularly excellent hard water resistance, and is useful for various utilities, for instance, as a surfactant, emulsifier, or the like, and a process for the production of the sulfonated product.

8 Claims, No Drawings

SULFONATED PRODUCT OF BUTADIENE OR ISOPRENE OLIGOMER AND THE PRODUCTION THEREFOR

BACKGROUND AND SUMMARY OF THE INVENTION

The present invention relates to a novel sulfonated product of a butadiene or isoprene oligomer and a process for the production thereof. More particularly, it relates to a sulfonated product of the following formula:

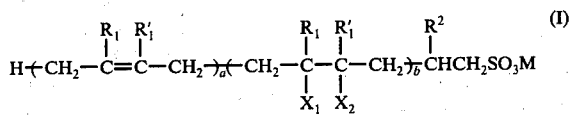

wherein one of $R_1$ and $R_1'$ is hydrogen or methyl and another one is hydrogen; $R_2$ is hydrogen or methyl; one of $X_1$ and $X_2$ is $-SO_3M$ and another one is hydrogen; $a$ and $b$ are each an integer satisfying the conditions: $n = a + b$, $2 < n < 40$ and $0 < b$; M is hydrogen, Na, K, Li or $-NR_3R_4R_5R_6$; and $R_3$, $R_4$, $R_5$ and $R_6$ are each hydrogen or an alkyl having 1 to 6 carbon atoms, and a process for the production of the sulfonated product.

Sulfonic acid is a strong acid comparable to hydrochloric acid and a salt of sulfonic acid is water-soluble. The sulfonic acid or a salt thereof can be used for giving some specific properties to organic compounds by reacting therewith, and hence, the sulfonic acid or its derivatives are very valuable as an intermediate for the preparation of compounds useful in surfactants or dyestuffs industries and other organic industries. Extensive research has hitherto been done on aromatic sulfonated products, but only a small amount of research has been done on aliphatic sulfonated products.

During the present inventors' studies on liquid butadiene and isoprene oligomers and derivatives thereof, they have aimed at the sulfonic acid derivative of these butadiene and isoprene oligomers which have specific properties and have made extensive studies on the process for the production thereof and also on the properties thereof. As the a result, it has been found that some novel sulfonated products of liquid polybutadiene show excellent properties as mentioned hereinafter, and further that some novel sulfonated products of isoprene oligomers also show excellent properties.

Some sulfonated products of polymers, such as a polymer of vinylsulfonic acid and a sulfonated product of polystyrene are known, but there is not known any other sulfonated product of a polymer having a chemically clear structure. For instance, some sulfonated products of polyolefins such as polyethylene, polypropylene or polyisobutene are described in Italian Patent Specification No. 591,501, but the sulfonation has been done for the purpose of accelerating the vulcanization of the high polymers and these compounds do not have a clear structure.

Some compounds similar to the sulfonated products, such as a sulfuric acid ester of polyvinyl alcohol, have also been known, but these compounds are an ester of an alcohol and sulfuric acid and are clearly distinguished from the sulfonated products.

An object of the present invention is to provide novel sulfonated products of butadiene or isoprene oligomer of the formula (I). Another object of the present invention is to provide a process for the production of the sulfonated products (I). These and other objects of the invention will be apparent from the following description.

The sulfonated products of the formula (I) can be produced by various processes, but is usually produced by first produced an oligomer of butadiene or isoprene and then sulfonating the oligomer.

It is known that highly unsaturated compounds such as polybutadiene are reacted with sulfites to give sulfonated products (cf. Japanese Patent Publication No. 6834/1974). In this process, polybutadiene containing a vinyl group in the side chain is used as the starting material. However, according to the present inventors' study, it is not necessarily required to use such a compound containing a double bond in the side chain. Generally, in the case of the reaction of high molecular weight compounds wherein the double bond participates, the reaction effectively proceeds when the double bond is contained in the side chain of the reactants. It has now been found that, even if the polymers having the double bond in the main chain, such as high 1,4-type polybutadiene, are used as the reactant, they can be sulfonated by reacting them with sulfites, and further that the sulfonated products thus obtained have various excellent properties as mentioned hereinafter.

Moreover, according to the present invention, when a polymer containing a terminal double bond in addition to the double bond in the main chain is used as the starting material, the positioning of the sulfonyl group in the molecule can be controlled by utilizing the difference of the reactivity between the double bond and the sulfites.

When the starting material is a polymer having repeating units of the same chemical structure containing a vinyl bond, as disclosed in Japanese Patent Publication No. 6834/1974, the addition reaction thereof with sulfites proceeds at random, and hence, the positioning of the sulfonyl groups can not be controlled and shows a statistical distribution. On the contrary, when the starting material is a polybutadiene having no vinyl group in the side chain, as in the present invention, there can be produced a sulfonated product wherein the sulfonyl group is preferentially combined to the terminal of the molecule. Moreover, according to the present invention, the double bonds contained in the main chain of the polybutadiene can almost be retained without reacting with the sulfites, and hence, the resulting sulfonated products have a specific structure containing unsaturated bonds in the main chain.

The addition reaction of sulfites to unsaturated bonds has been widely studied. The rate of the addition reaction of sulfites varies depending on the kinds of structures of the compounds containing double bond (cf. Charles J. Norton et al, The Journal of Organic Chemistry, page 4158, 1968). The reaction rate will be slower in the order as shown in the following scheme:

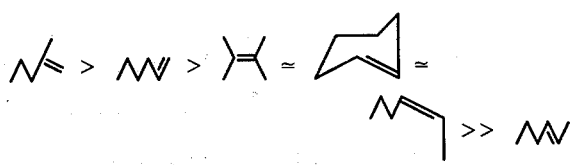

Taking into consideration these prior arts, the present inventors have succeeded in the production of novel sulfonated products by producing an oligomer of butadiene or isoprene which has no vinyl group in the side chain and then preferentially adding sulfites to the terminal double bond. It has never been known that such a sulfonated product can be produced by adding sulfites to the polymer having no double bond in the side chain without reacting the double bond in the main chain and thereby the positioning of the sulfonyl groups in the molecule can be controlled. Moreover, according to the present invention, the desired sulfonated products can easily be produced without complicated side reaction or significant coloring of the product and without using any specific apparatus.

The starting butadiene or isoprene oligomers used in the present invention may be produced by known processes as disclosed in Japanese Laid Open Publication (without examination) Nos. 89788/1974 and 115189/1974. The oligomers include the liquid butadiene or isoprene oligomers comprising predominantly the compound containing double bond in the main chain of the following formula:

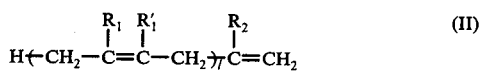

wherein one of $R_1$ and $R_1'$ is hydrogen or methyl and another one is hydrogen; $R_2$ is hydrogen or methyl; and $l$ is an integer satisfying the condition: $2 \leq l \leq 40$. $3 \leq l \leq 8$ is preferred because of the better power of emulsification.

These oligomers have the structure that ethylene or propylene is bonded to the terminal of a lower polymer of butadiene or isoprene.

The oligomers produced by the process have a wide range of molecular weight distribution and have larger contents of the compounds having a higher molecular weight than that of the compounds which are suitable for the preparation of synthetic detergents. When the sulfonated product of the present invention is used for the preparation of synthetic detergents, it is preferable to produce a product having a narrower molecular weight distribution by controlling the polymerization reaction so as to increase the reaction product having a lower degree of polymerization and further fractionating the reaction product. For instance, the oligomer produced by the process as hereinafter described in Example 1 contains predominantly the compound of the formula (II) wherein $R_1$ and $R_1'$ are each hydrogen and $R_2$ is methyl, and when this oligomer is subjected to rectification and gel permeation chromatography, the products as shown in the following Table 1 can be obtained.

Table 1

| $l$ in the formula (II) | Molecular* weight | Viscosity at 30° C (cp) | Boiling point (° C) | Specific gravity ($d^{25}$) | Refractive index ($n_D^{25}$) |
|---|---|---|---|---|---|
| 2 | 150 | 1.5 | 51 (2mmHg) | 0.770 | 1.449 |
| 3 | 204 | 4.3 | 93 (2 mmHg) | 0.797 | 1.458 |
| 4 | 260 | 5.2 | 156 (2 mmHg) | 0.821 | 1.486 |
| 5 | 340 | 10.4 | 210 (0.04 mmHg) | 0.867 | 1.504 |

The oligomer produced by the polymerization may be fractionated by a conventional method to give the first fraction (boiling point: not higher than 130° C./40 mmHg), the second fraction (boiling point: 60°–160° C./1 mmHg), and the residue, and the suitable fraction is used as the starting oligomer in accordance with the desired utility.

The sulfites used as another reactant in the present invention include hydrogensulfites, metasulfites or sulfites of alkali metals, alkaline earth metals, ammonia, organic amines or quaternary ammonium bases (e.g. sodium hydrogensulfite, potassium hydrogensulfite, calcium hydrogensulfite, ammonium hydrogensulfite, sodium metasulfite, potassium metasulfite, sodium sulfite, potassium sulfite, calcium sulfite, ammonium sulfite), which may be used alone or in a mixture thereof. Alkali metal salts (e.g. sodium, potassium or lithium salt) are usually used. These salts may be used in an amount of 1 mol to 2($l$ + 1) mol, wherein $l$ means the same as defined in the formula (II), to one mol of the oligomer in the sulfonation reaction, i.e. in a molar amount equivalent or double to the number of the double bond to which the sulfonyl group is introduced.

In the sulfonation of the oligomer in the present invention, a catalyst is not necessarily used, but use of an inorganic oxidizing catalyst is usually effective for shortening the reaction time. Suitable examples of the inorganic oxidizing catalyst are various metal salts of nitric acid, nitrous acid, chromic acid or chloric acid, such as alkali metal salts (e.g. sodium, potassium, lithium or rubidium salt), alkaline earth metal salts (e.g. beryllium, magnesium, calcium, zinc, cadmium or mercury salt), or other metal salts (e.g. iron, cobalt, nickel, chromium or aluminum salt) or ammonium salt. Among these salts, the salts of nitric acid are particularly effective. Oxygen or oxygen-containing gases are also useful as the catalyst. The catalyst is preferably used in an amount of 1/5 to 1/100 mol, more preferably 1/8 to 1/20 mol, to one mol of the starting sulfite.

The sulfonation of the present invention may be carried out in the absence or presence of a solvent, but it is preferable to conduct the reaction in an appropriate solvent for proceeding with the reaction both uniformly and smoothly. Suitable examples of the solvent are water, lower alcohols (e.g. methyl alcohol, ethyl alcohol, propyl alcohol, isopropyl alcohol, butyl alcohol, tert-butyl alcohol), lower glycols (e.g. ethylene glycol, propylene glycol), ketones (e.g. acetone, methyl ethyl ketone), ethers (e.g. ethylene glycol monomethyl ether, ethylene glycol monoethyl ether, ethylene glycol monobutyl ether, diethylene glycol monomethyl ether, dioxane), esters (e.g. ethyl acetate), or the like, which may be used alone or in a combination of two or more thereof. A mixed solvent of water and a lower alcohol, particularly water and propyl alcohol, is preferable. The amount of the solvent is not necessarily specified, but the ratio of solvent/oligomer may preferably be in the range of 10/1 to 1/1 by weight, more preferably 8/1 to 3/1 by weight. In case of using a mixed solvent of water and a lower alcohol, the ratio of alcohol/water may preferably be in the range of 10/1 to 1/1 by weight, more preferably 5/1 to 3/1 by weight.

When water or a mixed solvent of water and other organic solvent is used, the reaction proceeds at a pH value of 2 to 9, but it is preferable to control the pH value in the reaction system in the range of 5 to 7 by using a pH regulator in order to prevent undesirable side reaction and to decrease the production of inorganic salts.

The sulfonation may be carried out at a reaction temperature of 30° to 200° C., preferably 60° to 150° C., more preferably 90° to 120° C., under atmospheric pressure or under pressure. The sulfonation reaction is usually completed within 2 hours at 120° C. When a solvent is used, it is preferable to control the reaction conditions so that the solvent is maintained in liquid state.

In order to obtain the sulfonated products in the form of a free sulfonic acid derivative [i.e. M is hydrogen in the formula (I)], the reaction may be carried out at a low pH value. However, it will be preferable to desalt the sodium or potassium salt of the starting sulfites or the salt of the sulfonated product. The desaltation may be carried out by conventional methods, preferably dialysis or treatment with an ion exchange resin. For instance, a cationic exchange resin which is available commercially is introduced into a column and is modified into H type, and thereto an aqueous solution of a salt of a sulfonated product is continuously passed through, and thereby the salt of the sulfonated product can be converted into the free sulfonic acid derivative.

Besides, in order to obtain the sulfonated products in the form of an ammonium salt or quaternary ammonium salt of the formula: $-NR_3R_4R_5R_6$ wherein $R_3$, $R_4$, $R_5$ and $R_6$ are as defined above, the free sulfonic acid derivative obtained above is neutralized with aqueous ammonia or an aqueous solution of a quaternary ammonium hydroxide of the formula: $NR_3R_4R_5R_6(OH)$. Suitable examples of the quaternary ammonium hydroxide are tetramethyl ammonium hydroxide, tetraethyl ammonium hydroxide, tetrapropyl ammonium hydroxide, tetrabutyl ammonium hydroxide, or the like.

The sulfonated products thus obtained are usually white or faint yellow, solid or grease-like material, while it depends on the physical properties and molecular weight of the starting butadiene or isoprene oligomers and further on the numeral of the sulfonyl group combined thereto. Besides, the sulfonated products are usually easily soluble in water, soluble in polar solvents such as lower alcohols, or dimethylsulfoxide, and insoluble in other organic solvents. However, the solubility of the product may be variable depending on the various factors, such as the molecular weight of the starting oligomers, the numeral of the sulfonyl group combined thereto or the kind of cation which forms the salt, and there can also be produced a product which is insoluble in water and soluble in organic solvents.

The novel sulfonated products of the present invention have a specific chemical structure and specific properties and hence are valuable for various utilities.

For instance, the sulfonated products are useful as a surfactant for the preparation of emulsifiers, dispersing agents and wetting agents. The products contain many double bonds in the main chain thereof, and hence, they are easily decomposable and are valuable as a surfactant having no problem of environmental pollution.

The sulfonated products have a particularly excellent hard water resistance, and hence, when they are used for the preparation of synthetic detergents, they show an excellent effect as a builder. Thus, the products are valuable for the preparation of detergents having low phosphorus content and having no problem of environmental pollution. The excellent hard water resistance of the present sulfonated products may be owing to the same principle as that of α-olefin sulfonate which shows a higher resistance to hard water than that of an alkanesulfonate, i.e., owing to the mechanism that the heavy metals contained in the hard water are hindered between the double bond of the molecule and the sulfonyl group and the mechanism that the affinity to the dirt is improved by the integrity of the molecule due to the double bond in the molecule.

When the sulfonated products are used as an emulsifier for emulsion polymerization, the reactive double bond contained therein functions to combine with the polymer and thereby prevent the isolation of the emulsifier from the emulsion particles. Moreover, when the emulsion produced by using the sulfonated products as the emulsifier is used as a paint, the paint is crosslinked by air oxidization thereof during the forming of the coating film, and thereby, the water resistance of the coating film is improved.

Furthermore, when the sulfonated products are combined with high molecular weight compounds via the reactive double bond, owing to the polarity of the sulfonyl group contained in the products, they can give to the high molecular weight compounds various excellent properties, such as antistatic properties, conductivity, water absorption properties, dyeability and stainproofing properties, and hence, they can be used for various industrial utilities, such as plastics, fibers and printing materials, as well as paints.

The performances of the sulfonated products may optionally be varied by hydrogenating the starting oligomers or the sulfonated products in accordance with the desired utilities.

The present invention is illustrated by the following Examples but is not limited thereto.

EXAMPLE 1

Butadiene oligomer was produced as follows:

To a 100 ml flask provided with a stirring rotor were added dehydrated and deaerated toluene (20 ml), a solution of nickel naphthenate (0.2 mol/liter) in toluene (7.4 ml), butadiene (2 g), a solution of triethylaluminum (1 mol/liter) in toluene (14.8 ml), a solution of triphenylphosphine (0.167 mol/liter) in toluene (8.8 ml) and a solution of benzotrichloride (1 mol/liter) in toluene (7.4 ml), and the mixture was heated at 60° C. for 30 minutes to prepare a catalyst solution.

To a 3 liter stainless autoclave (compressive strength: 20 kg/cm$^2$) provided with a stirring blade were added dehydrated and deaerated toluene (400 g) and the catalyst solution prepared above. Thereto were added anhydrous distilled butadiene (50 g) and anhydrous propylene (100 g), and the mixture was heated up to 60° C. After the temperature of the mixture was raised to 60° C., to the 3 liter stainless autoclave (polymerization vessel) was added in portions, at an interval of 30 minutes, each 70 g of a mixture of butadiene and propylene which was previously prepared by adding anhydrous distilled butadiene (400 g) and anhydrous propylene (160 g) to a one liter stainless autoclave (compressive strength: 20 kg/cm$^2$). After polymerizing for 5 hours in total, the reaction mixture was cooled to room temperature and the unreacted propylene and butadiene were purged. A solution of isopropyl alcohol (2 mol/liter) in toluene (14.8 ml) was added to the resulting mixture, and then the mixture was stirred for 10 minutes to stop the polymerization reaction. The reaction product was moved to a beaker and was allowed to stand overnight, and the precipitated catalyst was removed by filtration.

The resulting reaction mixture was distilled under reduced pressure with an improved type Widmer spiral to concentrate the polymer and to fractionate it into three fractions (first to third fractions). The residue which remained after distilling at 178° C./2 mmHg was further distilled with a thin film, free flow type, molecular distillation apparatus, and then the fraction obtained at 210° C./0.04 mmHg was obtained as the fourth fraction. The results of the above fractionation are shown in the following Table 2.

Table 2

| Fraction | Conditions for the fractionation ° C | mmHg | Amount of fraction g | % by weight | Viscosity*[1] at 30° C (cp) | Molecular*[2] weight |
|---|---|---|---|---|---|---|
| First | 51–56 | 28–2 | 97.8 | 25.9 | 1.5 | 150 |
| Second | 61–98 | 2 | 86.65 | 22.9 | 4.3 | 205 |
| Third | 130–178 | 2 | 78.7 | 20.8 | 5.2 | 260 |
| Fourth | 210 | 0.04 | 67.6 | 19.5 | 10.4 | 340 |
| Residue | — | — | 37.45 | 10.8 | 33.7 | 408 |

Each fraction was subjected to gas chromatography and gel permeation chromatography, and thereby it was confirmed that the first fraction comprised the compound of the formula (II) wherein $l$ is 2, the second fraction comprised the compound of the formula (II) wherein $l$ is 3, the third fraction comprised the compound of the formula (II) wherein $l$ is 4, and the fourth fraction comprised the compounds of the formula (II) wherein $l$ is 5 and 6. It was also confirmed that the mixture has sufficiently been rectified from the results of measuring the molecular weight by the vapor pressure osmometer. According to infrared absorption spectrum analysis of each fraction, there was observed an absorption at 896 cm$^{-1}$ owing to vinylidene group instead of the absorption at 906 cm$^{-1}$ owing to vinyl group in 1,2-polybutadiene. Accordingly, it was confirmed that the produced polymer contained substantially no vinyl group in the side chain, but the terminal group of the molecule thereof was vinylidene group as shown in the formula (II).

Each fraction thus obtained was then sulfonated.

The first fraction was sulfonated as follows:

To a 1.5 liter stainless autoclave provided with a stirring blade and a thermometer were added the above first fraction (90 g), sodium hydrogensulfite (52 g), potassium nitrate (5.2 g), isopropanol (350 g) and distilled water (70 g). The mixture was reacted with strong stirring at 110° C. for 2 hours with closing the valve of the autoclave. After cooling to room temperature, distilled water (300 ml) was added to the reaction mixture, and the mixture was stirred and was separated into two layers.

The upper layer (oily layer) was separated and was concentrated, and thereby, unreacted liquid polybutadiene (47.2 g) was recovered therefrom. The lower layer was concentrated with an evaporator to remove the solvent. To the residue were added petroleum ether (150 ml), distilled water (150 ml) and ethyl cellosolve (35 ml). The mixture was sufficiently stirred and then allowed to stand to separate into two layers. When the upper layer was concentrated, unreacted liquid polybutadiene (2.4 g) solubilized into the sulfonated product was recovered. To the lower layer was further added ethyl cellosolve (120 ml), and the mixture was separated into two layers, likewise. By concentrating each layer, there were obtained white yellow solid material (A) (26.4 g) from the upper layer and white powdery material (B) (9.2 g) from the lower layer. These materials were purified by extraction with ethanol and were subjected to elemental analysis. As a result, the analysis of (A) was C,51.76%; H,7.50%; S,12.48%. The infrared absorption spectrum of (A) was measured in the form of KBr tablet. As a result, the absorption at 896 cm$^{-1}$ owing to the vinylidene group in the starting polymer disappeared, and instead thereof, there were observed the absorptions at 1180 cm$^{-1}$, 1040 cm$^{-1}$ and 620 cm$^{-1}$ owing to the sulfonyl group, from which it was confirmed that the terminal vinylidene group was sulfonated. It was also confirmed from the sulfur content of the above elemental analysis that one sulfonyl group was combined per one molecule of the polymer. The sulfonated product has a softening point of 168° C. and a decomposition point at 180° C.

This solid material is hydroscopic and is easily soluble in water (solubility: more than 100 at 0° C.).

As a result of the conductometric analysis, it had a critical micelle concentration of 0.12% by weight at 25° C. and a surface tension of 36.9 dyne/cm (25° C.) in a concentration of 2% by weight.

EXAMPLES 2 to 4

Other three fractions obtained in Example 1 were sulfonated in the same manner as described in Example 1.

To the same reactor as used in Example 1 were charged each reactant as shown in the following Table 3 and were added thereto isopropyl alcohol (700 g) and distilled water (140 g), and the mixture was reacted at 110° C. for 2 hours. After the reaction, the reaction mixture was concentrated with an evaporator to remove the solvent. To the residue were added petroleum ether (200 ml), distilled water (200 ml) and butyl cellosolve (30 ml), and the mixture was sufficiently stirred and was allowed to stand to separate into two layers.

The upper layer was concentrated and thereby unreacted liquid polybutadiene was recovered. To the lower layer was further added butyl cellosolve (200 ml), and the mixture was stirred and allowed to stand to sepratate into two layers, likewise. There were obtained crude sulfonated polybutadiene from the upper layer and unreacted inorganic salts from the lower layer. The crude product was extracted with petroleum ether (200 ml) at reflux temperature for 15 hours in Soxhlet apparatus to remove the unreacted liquid polybutadiene solubilized into the sulfonated product. The resultant was dissolved in aqueous ethanol to remove the precipitated sodium sulfate which was produced by the side reaction.

The sulfonated polybutadiene thus purified was subjected to various analyses as in Example 1. The results are shown in Table 3.

Table 3

| Ex. No. | Reactants Polybutadiene Fraction No. | g | NaHSO$_3$ | KNO$_3$ | Yield of sulfonated polybutadiene (g) | Elemental analysis (%) C | H | S | Numeral of sulfonyl group in one molecule | Surface* tension (dyne/cm) |
|---|---|---|---|---|---|---|---|---|---|---|
| 2 | Second | 80 | 40.78 | 4.078 | 32.4 | 41.92 | 6.47 | 14.86 | 1.8 | 40.5 |
| 3 | Third | 60 | 27.1 | 2.71 | 35.6 | 49.27 | 7.16 | 10.73 | 1.3 | 45.8 |
| 4 | Fourth | 50 | 15.6 | 1.56 | 19.4 | 50.32 | 7.38 | 11.55 | 2.0 | 48.6 |

*It was measured at 25° C in a concentration of 2 % by weight.

EXAMPLE 5

Butadiene oligomer was produced as follows:

To a 100 ml flask provided with a stirring rotor were added anhydrous toluene (20 ml), a solution of nickel naphthenate (0.2 mol/liter) in toluene (4.5 ml), butadiene (2 g), a solution of triethylaluminum (1 mol/liter) in toluene (9 ml), a solution of triphenylphosphine (0.167 mol/liter) in toluene (5.4 ml) and a solution of benzotrichloride (1 mol/liter) in toluene (4.5 ml), and the mixture was heated at 60° C. for 30 minutes to prepare a catalyst solution.

To a 3 liter stainless autoclave (compressive strength: 20 kg/cm$^2$) provided with a stirring blade were added the catalyst solution prepared above and further anhydrous toluene (300 ml), anhydrous propylene (153.6 g) and anhydrous distilled butadiene (110 g), and the mixture was polymerized at 60° C. for 4.5 hours. After the reaction, the reaction mixture was cooled to room temperature, and the unreacted propylene and butadiene were purged. A solution of isopropyl alcohol (2 mol/liter) in toluene (9 ml) was added to the resulting mixture and the mixture was stirred for 10 minutes to stop the polymerization reaction. The reaction mixture was allowed to stand in air overnight, and the precipitated catalyst was removed by filtration. The filtrate was distilled under reduced pressure to remove lower polymers having a lower boiling point and the solvent (toluene), and thereby, there was obtained transparent liquid (112 g) having a low viscosity of 2.2 cp at 30° C. When the molecular weight of the product was measured with a vapor pressure osmometer, it had a number average molecular weight of 253.6. The polymer was fractionated to give the first fraction (boiling point: not higher than 130° C./40 mmHg, 42.5 g), the second fraction (boiling point: 60°-160° C./1 mmHg, 38.6 g) and remaining residue (30.9 g). The number average molecular weight and the micro structure of each fraction were measured with a vapor pressure osmometer and by infrared spectrum analysis. The results are shown in the following Table 4.

Table 4

| Fraction | Number average molecular weight | Micro structure | | |
|---|---|---|---|---|
| | | 1,4-cis | 1,4-trans | Vinylidene |
| First | 182 | 31 | 51 | 18 |
| Second | 254 | 34 | 54 | 12 |
| Residue | 480 | 38 | 53 | 9 |

According to infrared absorption spectrum analysis, there was observed an absorption at 896 cm$^{-1}$ owing to vinylidene group instead of the absorption at 906 cm$^{-1}$ owing to vinyl group in 1,2-polybutadiene, from which it was confirmed that the produced polymer contained substantially no vinyl group in the side chain.

To a 100 ml stainless autoclave provided with a stirring blade and a thermometer were added the above second fraction (10 g), sodium hydrogensulfite (4.03 g), potassium nitrate (0.39 g), isopropanol (40 g) and water (7.5 g). The mixture was reacted with strong stirring at 110° C. for 6 hours with closing the valve of the autoclave. After cooling to room temperature, water (200 ml) was added to the reaction mixture, and the autoclave was shaken to separate the mixture into two layers. The lower layer (transparent yellow liquid) was taken out and regulated to a pH value of 8 and then concentrated under reduced pressure to give a faint yellow solid material (7.95 g). The faint yellow solid material was extracted with petroleum ether (100 ml) at reflux temperature for 15 hours in Soxhlet apparatus to remove the unreacted liquid polybutadiene solubilized into the sulfonated product. The resulting crude product (5.95 g) was extracted with ethanol and thereby the insoluble inorganic materials were removed. The final yield of the product was 3.8 g.

The product thus purified was white, hygroscopic sold material. According to infrared absorption spectrum analysis, the absorption at 896 cm$^{-1}$ owing to the vinylidene group in the starting polymer disappeared, and instead thereof, there were observed the absorptions at 1200 cm$^{-1}$, 1050 cm$^{-1}$ and 610 cm$^{-1}$ owing to the sulfonyl group, from which it was confirmed that the terminal vinylidene group was sulfonated. According to elemental analysis, it contained 8.9% of sulfur, from which it was confirmed that one sulfonyl group in average was combined per one molecule of the polymer. The sulfonated product has a softening point of about 168° C. and a decomposition point of 180° C.

As a result of conductometric analysis, it had a critical micelle concentration of 0.15% by weight at 25° C. and a surface tension of 45.0 dyne/cm (25° C.) in a concentration of 2% by weight.

EXAMPLE 6

Isoprene oligomer was produced as follows:

To a 100 ml flask provided with a stirring rotor were added anhydrous toluene (20 ml), a solution of nickel naphthenate (0.2 mol/liter) in toluene (3.64 ml), anhydrous distilled isoprene (2 g), a solution of ethylaluminum sesquichloride (0.909 mol/liter) in toluene (8.0 ml) and a solution of triphenylphosphine (0.02 mol/liter) in toluene (7.27 ml), and the mixture was stirred at 30° C. for 30 minutes to prepare a catalyst solution.

To a 1.5 liter stainless autoclave (compressive strength: 20 kg/cm$^2$) provided with a stirring blade were added the catalyst solution prepared above and further anhydrous toluene (190 ml), anhydrous distilled isoprene (270 g) and anhydrous propylene (68 g), and the mixture was polymerized at 60° C. for 7 hours. The polymerization reaction was stopped in the same manner as described in Example 1, and the solvent was distilled therefrom to give a polymer (229.5 g) having a viscosity of 13.3 cp at 30° C.

The polymer thus obtained was fractionated with the same apparatus as used in Example 1. By subjecting each fraction to gas chromatography and gel permeation chromatography, it was confirmed that the first fraction comprised a compound consisting of two units of isoprene and one unit of propylene, the second fraction comprised a compound consisting of three units of isoprene and one unit of propylene, and the third fraction comprised a compound consisting of four units of isoprene and one unit of propylene. Various properties of each fraction are shown in the following Table 5.

Table 5

| Fraction | Condition for the fractionation | | Amount of fraction | | Viscosity at 30° C (cp) | Molecular* weight | Specific gravity (d$^{25}$) | Refractive index (n$_D^{25}$) |
|---|---|---|---|---|---|---|---|---|
| | ° C | mmHg | g | % by weight | | | | |
| First | 50-100 | 2 | 12.8 | 5.6 | 3.2 | 182 | 0.782 | 1.428 |
| Second | 110-165 | 2 | 32.3 | 14.1 | 4.7 | 250 | 0.796 | 1.441 |
| Third | 200 | 0.04 | 51.8 | 22.6 | 8.5 | 321 | 0.827 | 1.453 |

Table 5-continued

| Fraction | Condition for the fractionation °C | mmHg | Amount of fraction g | % by weight | Viscosity at 30° C (cp) | Molecular* weight | Specific gravity ($d^{25}$) | Refractive index ($n_D^{25}$) |
|---|---|---|---|---|---|---|---|---|
| Residue | — | — | 132.6 | 57.8 | 37.8 | 582 | 0.861 | 1.467 |

*It was measured by a vopor pressure osmometer.

Each fraction was sulfonated in the same manner as described in Example 1.

Sulfonation of the second fraction obtained above was carried out under the following conditions:

To a 400 ml stainless autoclave were added liquid polyisoprene (30 g), sodium hydrogensulfite (8 g), potassium nitrate (0.7 g), isopropanol (100 g) and water (18 g), and the mixture was reacted at 110° C. for 6 hours after closing the valve of the autoclave. After the reaction, the reaction mixture was cooled to room temperature and thereto was added petroleum ether (200 ml) and the mixture was well mixed. After removing the petroleum ether and the precipitates, the remaining solution was concentrated. The yellow viscous liquid (16 g) thus obtained was well admixed with petroleum ether and water, and the mixture was allowed to stand to separate into two layers. The aqueous layer was carefully concentrated, while it was foamed, and thereby, there was obtained faint yellow solid material (11.5 g).

By the infrared absorption spectrum analysis, it was confirmed that the solid material was the desired sulfonated product and further that the sulfonyl group was combined to the terminal thereof from the fact that the absorption owing to vinylidene group disappeared. According to elemental analysis, it contained 9.1% of sulfur, from which it was confirmed that one sulfonyl group was combined per one molecule of the polymer. The sulfonated product has a softening point of 160°–165° C.

As a result of conductometric analysis, it had a critical micelle concentration of 0.5% by weight at 25° C.

EXAMPLE 7

Butadiene oligomer combined with ethylene was produced as follows:

To a 100 ml flask provided with a stirring rotor were added dehydrated deaerated toluene (10 ml), a solution of nickel naphthenate (0.2 mol/liter) in toluene (1.5 ml), butadiene (1 g), a solution of triethylaluminum (1 mol/liter) in toluene (3 ml), a solution of triphenylphosphine (0.167 mol/liter) in toluene (1.8 ml) and a solution of benzotrichloride (1 mol/liter) in toluene (1.5 ml), and the mixture was stirred at 60° C. for 30 minutes to prepare a catalyst solution.

To a 1.5 liter stainless autoclave (compressive strength: 20 kg/cm²) provided with a stirring blade were added dehydrated deaerated toluene (206 g) and the catalyst solution prepared above. To the mixture was further added anhydrous butadiene (58 g) and the valve of the autoclave was closed. After stopping the cooling of the autoclave, the mixture was heated up to 20° C., during which ethylene was introduced thereto from an ethylene bomb. The mixture was reacted at 20° C. under a pressure of 4.5 kg/cm² for 4 hours in total. After purging unreacted butadiene and ethylene, the polymerization reaction was stopped. The reaction mixture was concentrated to give a liquid polymer (44 g) having a viscosity of 10 cp at 25° C. which was measured with a falling ball viscometer. The polymer thus obtained was fractionated with the same apparatus as used in Example 1. The results are shown in the following Table 6.

Table 6

| Fraction | Conditions for the fractionation °C | mmHg | Amount of fraction g | % by weight | Molecular* weight | Specific gravity ($d^{25}$) | Refractive index ($n_D^{25}$) |
|---|---|---|---|---|---|---|---|
| First | 70–87 | 6 | 7.2 | 16.4 | 138 | 0.765 | 1.442 |
| Second | 80–82 | 0.6 | 8.6 | 19.5 | 196 | 0.792 | 1.454 |
| Third | 86–145 | 0.35 | 6.4 | 14.5 | 250 | 0.819 | 1.480 |
| Residue | — | — | 11.0 | 25.0 | 476 | 0.889 | 1.492 |

*The molecular weight was measured with a vapor pressure osmometer.

The polymer showed a peak at 906 cm$^{-1}$ in the infrared absorption spectrum, which means that vinyl group derived from ethylene is present at the terminal of the molecule. NMR spectrum of each fraction was measured. The results are shown in the following Table 7.

Table 7

| | | Number of proton τ value | | | | |
|---|---|---|---|---|---|---|
| | | 4.7 | 5.37 | 7.38 | 8.0 | 8.33 |
| First fraction | Found | 5 | 1.8 | 2.2 | 4 | 3 |
| | Calcd. ($C_{10}H_{16}$) | 5 | 2 | 2 | 4 | 3 |
| Second fraction | Found | 7.2 | 1.9 | 2.2 | 7.7 | 3 |
| | Calcd. ($C_{14}H_{22}$) | 7 | 2 | 2 | 8 | 3 |
| Third fraction | Found | 9.1 | 1.8 | 2.3 | 11.6 | 3.2 |
| | Calcd. ($C_{18}H_{28}$) | 9 | 2 | 2 | 12 | 3 |

[Remarks]: (1) The groups from which proton is led with respect to each τ value are shown in the following Table 8.

Table 8

| τ value | 4.7 | 5.37 | 7.38 | 8.0 | 8.33 |
|---|---|---|---|---|---|
| Kind of groups | —CH=CH— | $CH_2$=C— | =$CCH_2$C= | —$CH_2$—C= | $CH_3$C= |

(2) The calculated value in Table 7 was calculated by assuming that the first fraction is n = 2, the second fraction is n = 3 and the third fraction is n = 4 in the formula: H–(–$CH_2$—CH=CH—$CH_2$–)$_n$ CH=$CH_2$.

By subjecting each fraction to gas chromatography and gel permeation chromatography, it was confirmed that each fraction comprised a single component.

On the basis of the results of the above analysis, it was clear that the first fraction comprised a compound consisting of two units of butadiene and one unit of ethylene, the second fraction comprised a compound consisting of three units of butadiene and one unit of ethylene, and the third fraction comprised a compound consisting of four units of butadiene and one unit of ethylene.

Each fraction was sulfonated in the same manner as described in Example 1.

The sulfonation of the third fraction was carried out under the following conditions:

To a 400 ml stainless autoclave were added liquid polymer (the third fraction) (5 g), potassium hydrogensulfite (1.5 g), potassium nitrate (0.2 g), butyl cellosolve (100 g) and distilled water (20 g), and the mixture was reacted at 110° C. for 2 hours with closing the valve of the autoclave. After removing most butyl cellosolve and water with an evaporator, distilled water (200 ml) and petroleum ether (100 ml) were newly added, and the mixture was well mixed.

The aqueous layer was separated therefrom and was concentrated. The precipitated white solid material was extracted with aqueous ethanol to give a white yellow solid material (2 g). By the infrared absorption spectrum analysis, it was confirmed that the solid material was the desired sulfonated product and further that the sulfonyl group was combined to the terminal thereof from the fact that the absorption at 906 cm$^{-1}$ owing to vinyl group disappeared. According to elemental analysis, it contained 13.7% of sulfur, from which it was confirmed that two sulfonyl groups were combined per one molecule of the polymer.

The sulfonated product has a softening point of 170°–175° C. As the result of conductometric analysis, it had a critical micelle concentration of 0.1% by weight at 25° C. When aqueous solutions of this sulfonated product (concentration: 0.005 to 0.5% by weight) were subjected to a test for hard water resistance, no precipitate was produced even when the concentration of calcium chloride was increased up to 1 mol, and further, no change was observed even when the temperature of the solution was lowered to 0° C.

What is claimed is:

1. A compound of the formula:

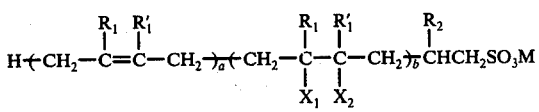

wherein one of $R_1$ and $R_1'$ is hydrogen or methyl and another one is hydrogen; $R_2$ is hydrogen or methyl; one of $X_1$ and $X_2$ is $-SO_3M$ and another one is hydrogen; $a$ and $b$ are each an integer satisfying the conditions: $n = a + b$, $2 \leq n \leq 40$ and $0 \leq b$; M is hydrogen, Na, K, Li or $-NR_3R_4R_5R_6$; and $R_3$, $R_4$, $R_5$ and $R_6$ are each hydrogen or an alkyl having 1 to 6 carbon atoms.

2. The compound according to claim 1, wherein $b = 0$ and $R_2$ is hydrogen.

3. The compound according to claim 1, wherein $b = 0$ and $R_2$ is methyl.

4. The compound according to claim 1, wherein $b = 1$ and $R_2$ is hydrogen.

5. The compound according to claim 1, wherein $b = 1$ and $R_2$ is methyl.

6. The compound according to claim 1, wherein $b = 2$ and $R_2$ is hydrogen.

7. The compound according to claim 1, wherein $b = 2$ and $R_2$ is methyl.

8. The compound according to claim 1, wherein $b = 3$ and $R_2$ is hydrogen.

* * * * *